United States Patent
Finkielsztein et al.

(10) Patent No.: US 10,206,683 B2
(45) Date of Patent: Feb. 19, 2019

(54) METHODS AND APPARATUS FOR A MANUAL VASCULAR COMPRESSION DEVICE

(75) Inventors: Sergio Finkielsztein, Newton, MA (US); Marco Finkielsztein, Newton, MA (US); John N. Vournakis, Charleston, SC (US)

(73) Assignee: MARINE POLYMER TECHNOLOGIES, INC., Danvers, MA (US)

( * ) Notice: Subject to any disclaimer, the term of this patent is extended or adjusted under 35 U.S.C. 154(b) by 1018 days.

(21) Appl. No.: 11/092,369

(22) Filed: Mar. 29, 2005

(65) Prior Publication Data

US 2006/0229662 A1    Oct. 12, 2006

(51) Int. Cl.
A61B 17/08   (2006.01)
A61D 1/00    (2006.01)
A61B 17/12   (2006.01)

(52) U.S. Cl.
CPC .... *A61B 17/12* (2013.01); *A61B 2017/12004* (2013.01)

(58) Field of Classification Search
CPC ............... A61B 17/12; A61B 17/1325; A61B 2017/12004; A61F 5/30
USPC ..................................... 606/201–204.55, 215
See application file for complete search history.

(56) References Cited

U.S. PATENT DOCUMENTS 575,103 A * 1/1897 Burton .......................... 606/201
3,228,392 A   1/1966 Speyer
3,411,505 A * 11/1968 Nobis .......................... 606/201
3,884,240 A   5/1975 Gilman
4,109,649 A * 8/1978 Iyomasa ................. A61H 15/00
                                                                        601/121

(Continued)

FOREIGN PATENT DOCUMENTS

AT    295027 B    12/1971
GB    12486 A     0/1910

OTHER PUBLICATIONS

Examination Report from related Australian Application No. 2006230231 dated Oct. 25, 2010.

(Continued)

*Primary Examiner* — Melanie R Tyson
(74) *Attorney, Agent, or Firm* — Nutter McClennen & Fish LLP

(57) ABSTRACT

A vascular compression apparatus and method for applying pressure onto an area of a patient generally including a blood vessel and a wound site, such as a blood vessel puncture, after a cannulated procedure for the purpose of controlling bleeding and achieving hemostasis. The vascular compression apparatus includes a handle, a shaft and a pad. The shaft extends generally downward from the center of the bottom side of the handle. The pad is connected generally off-center of its top side to the bottom end of the shaft. The bottom side of the pad is convex to allow the vascular compression device to be rocked back and forth. In use, the pad is generally placed proximal to the catheter insertion site and over the blood vessel containing the catheter. The device is rocked proximally to control blood flow while removing the catheter. After the catheter is removed from the puncture site, the device is rocked distally to the puncture site, where pressure is applied until hemostasis is achieved.

12 Claims, 2 Drawing Sheets

(56) References Cited

U.S. PATENT DOCUMENTS

| | | | |
|---|---|---|---|
| 4,572,182 A | | 2/1986 | Royse |
| 5,050,902 A | | 4/1991 | Rambo et al. |
| 5,133,734 A | | 7/1992 | Lee |
| 5,263,965 A | | 11/1993 | Roth |
| 5,342,388 A | | 8/1994 | Toiler |
| 5,554,168 A | | 9/1996 | Petersen |
| 5,569,297 A | * | 10/1996 | Makower ............ A61B 17/1325 606/201 |
| D387,174 S | * | 12/1997 | Gladieux, Jr. ................ D24/211 |
| 5,762,173 A | | 6/1998 | Nishimura |
| 5,792,173 A | | 8/1998 | Breen et al. |
| 5,873,890 A | | 2/1999 | Porat |
| 5,997,564 A | | 12/1999 | Schehata et al. |
| 6,004,343 A | | 12/1999 | Kurth |
| D475,141 S | * | 5/2003 | Shin ............................. D24/214 |
| 2003/0028214 A1 | * | 2/2003 | Benz et al. .................... 606/201 |
| 2003/0105487 A1 | * | 6/2003 | Benz .................... A61B 17/132 606/201 |
| 2003/0114881 A1 | * | 6/2003 | Stalemark et al. ............ 606/201 |
| 2004/0176796 A1 | * | 9/2004 | Akerfeldt et al. ............. 606/201 |
| 2006/0095073 A1 | * | 5/2006 | Beto et al. .................... 606/201 |
| 2006/0229664 A1 | | 10/2006 | Finkielsztein et al. |

OTHER PUBLICATIONS

Extended European Search Report for Application No. 06739894.1 dated Jul. 8, 2013 (7 Pages).

\* cited by examiner

METHODS AND APPARATUS FOR A MANUAL VASCULAR COMPRESSION DEVICE

FIELD OF THE INVENTION

This invention relates in general to a manual vascular compression device and in particular to a manual femoral compression device.

BACKGROUND OF THE INVENTION

This invention relates to a vascular compression apparatus and method for controlling bleeding and achieving hemostasis by applying pressure onto an area of a patient including a wound site, such as a blood vessel puncture, and a blood vessel. In particular, this invention relates to a vascular compression device and a method for controlling bleeding and facilitating hemostasis following percutaneous catheterization via the femoral artery or vein.

The femoral artery is a high pressure blood vessel which generally requires direct pressure to achieve hemostasis (cessation of bleeding) following completion of a catheterization or cannulation procedure. If, for example, a sheath is removed from the femoral artery in the groin and no attempt to stem the bleeding is made, the patient would quickly experience severe bleeding which would resort in significant consequences including hypovolemia, shock, and possibly death. Hemostasis can often be achieved by applying pressure directly over the femoral artery as well as proximal and medial to the femoral artery puncture site, where such pressure slows or completely occludes blood flow in the artery. This permits a clot to form which causes hemostasis at the puncture site.

Traditionally, to achieve sufficient pressure, an individual must actively press down directly over the artery and proximal and medial to the puncture site for a period of time which varies based on the type of procedure, the nature of the drugs administered and the patient's condition—often for 30 minutes or longer. This can result in fatigue, stiffness and/or pain in the fingers, hands, wrist and forearms of the individual performing the procedure. Prolonged or repeated performance of this procedure may result in a repetitive stress injury such as carpal tunnel syndrome. The direct pressure method also puts the individual administering pressure at risk for direct exposure to the patient's blood.

Various types of automated manual solutions have been developed to, in part, address these issues. One example of an automated solution is shown by Petersen in U.S. Pat. No. 5,554,168. Petersen describes a free standing apparatus which may be attached to the bottom frame of a hospital bed. A pressure applying head is mounted on a swing arm attached to the vertical shaft of the base and can be positioned directly above the wound. Pressure is developed by either compressed air or an electric motor. Two pressure shoes can be positioned to provide both vertical and horizontal pressure.

Another automated solution is described by Lee in U.S. Pat. No. 5,133,734. Lee discloses a pneumatically operated femoral artery compressor applying calibrated and calibrateable external pressure on the puncture site of the femoral artery with the plunger end of a mounted pressurized assembly.

Breen et. al describe another type of partly automated solution, which also uses pneumatic pressure, in U.S. Pat. No. 5,762,173. Breen describes a wound closure device that includes an inflatable balloon with an inflation and deflation outlet. The balloon is coupled to patch, having an aperture for receiving the inflation/deflation outlet. The assembly is coupled to the placement patch and is held via a belt strap at either the wound site or on a bleeding vessel.

These automated compression devices are far from ideal, however. They tend to be expensive, difficult to maintain in good working order, consume a great deal of space and are difficult to keep sterile.

A number of manual compression devices have been described as well. Roth, in U.S. Pat. No. 5,263,965, describes a device that is used to apply direct pressure to arterial and venous incisions to promote hemostasis. It consists of a round flat disk with a user manipulable member used for applying downward pressure. In the preferred embodiment of the invention, the user manipulable member consists of a peg over which a cylindrical weight is pivotally mounted. A stretchable bandage is used to secure the weight in place.

Another type of manual compression device is described by Toller in U.S. Pat. No. 5,342,388. This manual compression aid is comprised of a cylindrically shaped handle above a sterile disposable disk. The disk is placed above the catheter insertion point with the catheter inside the notch of the disk. As the catheter is removed, pressure is applied to the handle to force the disk to compress the artery and thereby control bleeding—ultimately achieving hemostasis. This type of device has a number of disadvantages including: the cost of the apparatus; the difficulty associated in ensuring a minimal level of cleanliness; and the time associated in connecting the disposable disk to the assembly prior to its use on a patient.

Benz et. al describe another form of manual compression device in Pub No. US 2003/0028214. This manual vascular compression device also includes a handle an elongated shaft and a pad or disk. In this device the pad or disk is integral to the assembly and the entire apparatus is disposable. Like the pad of Toller, the pad is flat and contains a notched or equivalent area for locating the catheter.

All these devices, however, provide for straight vertical compression at a single location. This type of compression provides for suboptimal control of the artery or vein ultimately extending the time for achieving hemostasis.

SUMMARY OF THE INVENTION

The invention provides for an improved manual apparatus for assisting a user in controlling bleeding and achieving hemostasis. The invention more particularly provides for a manual vascular compression device.

An object of the invention is to assist a user in controlling bleeding and achieving hemostasis with a hand held device that allows for compression of a puncture site at both the skin level and blood vessel level simultaneously.

A further object of the invention is to assist a user in controlling bleeding and achieving hemostasis after removing a catheter or cannula from a blood vessel by providing for compression along the angle of the catheter or cannula track from the skin, to the blood vessel, rather than traditional straight vertical compression.

A further object of the invention is to provide for a manual femoral compression device that facilitates hemostasis following percutaneous catheterization via the femoral artery or vein.

These and other objects are achieved with the vascular compression apparatus described herein. The vascular compression apparatus is comprised of a handle, a shaft, and a pad. The proximal end of said shaft connects to said handle generally off-center of the bottom side of the handle. Said pad connects to the distal end of the shaft generally in the center of the top side of the pad. The bottom-side of the pad is slightly convex or curved in a manner that allows the user to rock the device proximally, for proximal control of blood flow while retrieving a device such as a catheter from a puncture site, followed by distal rocking of the device to the puncture site to achieve hemostasis. By providing varying degrees of pressure the user can alternatively compress the puncture site at the skin level and at the blood vessel level as well.

The pad, unlike a number of the prior art pads, contains no notch to enable proper placement of the of the vascular compression apparatus onto the body surface in proximity to a puncture site. In a preferred embodiment of the invention, the vascular compression device is made of a transparent or translucent material and a visual guide is provided, which overlies the blood vessel for which compression is desired, and follows the path of the blood vessel. In addition, the transparent or translucent material permits visualization of, and access to, the puncture site while compression is being applied. In a most preferred embodiment a grooved guide is provided to allow alignment of the catheter.

Additionally, because the pad is slightly elongated and the handle is off-center, the user can optionally place their other hand on either the top side of the pad or on the handle of the device to help stabilize the device and provide for additional pressure if necessary.

In one embodiment, the handle and elongate shaft of the vascular compression apparatus are formed as a single member and the pad is removably connected to the elongate shaft. In a preferred embodiment the pad is a nitary piece. In another preferred embodiment the pad is comprised of two or more components each of which is removably connected to either the elongated shaft or to another component of the pad.

In another preferred embodiment, the vascular compression apparatus is formed as a unitary member with the pad permanently connected to the elongate shaft, thereby requiring no assembly or disassembly by the user and which further allows for easy and complete sterilization. In a most preferred embodiment the unitary vascular compression apparatus is disposable.

Optionally the invention may be used with an external vascular closure device. Traditionally a simple pad or bandage can be used with the invention to aid in hemostasis. The bandages may come in various forms and include a standard gauze pad, a U.S. Army First Aid Field Bandage or other types of bandages. Recently new types of externally applied vascular closure devices have been developed that further decrease the time to hemostasis following catheterization. These include products that are based on a variety of macromolecules such as collagen, cellulose, chitosan and Poly-N-Acetyl Glucosamine (PGlcNAc). Commercially available products include: Actifoam™ (C. R. Bard, Inc. Murray Hill, N.J.), a collagen sponge; Surgicel (J&J Medical, Arlington, Tex.), a cellulose based product; Clo-Sur PAD™ (Scion Cardio-Vascular, Miami, Fla.), and Chito-Seal (Abbot Laboratories, Abbot Park, Ill.), both chitosan based products; and SyvekPatch® a pGLcNAc based product. Most preferably, the device is used with a SyvekPatch®.

Furthermore, the invention contemplates a kit comprising the manual femoral compression apparatus and an external vascular closure device. The kit is preferably sterile In a most preferred embodiment the components of the kit are disposable.

DETAILED DESCRIPTION OF THE INVENTION

Figure 1:
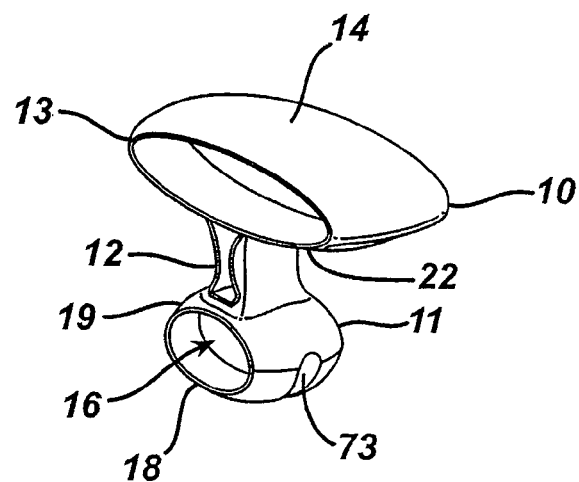
FIG. 1 is a perspective view of the invention.

To more clearly set forth the invention, reference will be made to the embodiments illustrated in the drawings and specific language will be used. Nevertheless, it should be understood that the invention should not be deemed limited to particular embodiments, descriptions or drawings contained herein.

The vascular compression apparatus of the invention is used on a patient to apply pressure on an area near or at a wound site, such as a blood vessel puncture, most often after a cannulated procedure such as angioplasty, for the purpose of controlling the patient's bleeding and, further, of achieving hemostasis.

FIG. 1 shows the manual vascular compression device of the invention 10. The device has a handle 13 having a top 14 and a bottom 22, a shaft 12 and a pad 11. The handle 13 is connected, generally off-center, to the proximal end of the shaft 12. The pad 11 is connected to the distal end of the shaft 12 and is generally centered on the top surface 19 of the pad 11. The handle 13 is generally elongated and may include solid or, as pictured, substantially hollow sides. The bottom 18 of the pad 11 is generally convex to allow for rocking of the device. In a preferred embodiment, the top 19 of the pad 11 is also convex.

FIG. 1 further shows the handle 13 as generally elongated. In a preferred embodiment the bottom 22 of the handle is slightly convex. When downward pressure is applied by a user on the handle 13 such pressure is transferred through the shaft 12 to the pad 11. The pad 11 depresses the area of the body surface upon which it rests, thereby compressing either the lumen of the blood vessel over which it is placed to partially or completely occlude the blood vessel or directly on a blood vessel puncture site to achieve hemostasis. In a preferred method of the invention, the user places the device over the puncture site and rocks the device 10 proximal to the puncture site and applies pressure for proximal control of blood flow while retrieving a medical device, such as a catheter, from the site. The user then distally rocks the device to the puncture site and applies pressure to achieve hemostasis.

Figure 2:
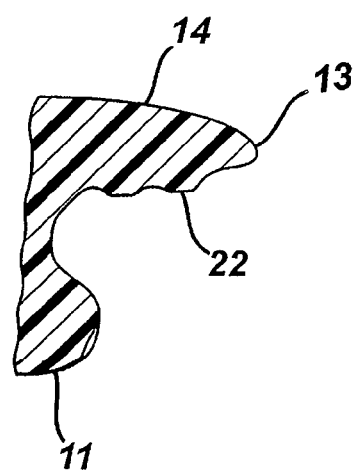
FIG. 2 is a side sectioned view of the invention shown in FIG. 1.
Figure 4:
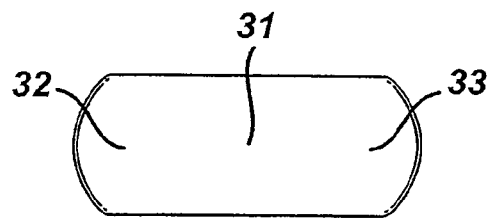
FIG. 4 is a bottom view of the pad of the invention.
Figure 3:
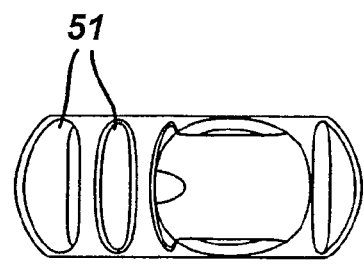
FIG. 3 is a top view of the invention.

FIG. 2 shows a side sectioned view of the invention.
FIG. 3 shows a bottom view of the device 10.
FIG. 4 shows a top view 14 of the handle 13. A vessel alignment guide 31 is provided to help the user align the device with the blood vessel and ultimately provide for compression following the angle of a catheter track. Visual guides are also provided to indicated the location of the patient's feet 32 or head 33 relative to the device.

Figure 5:
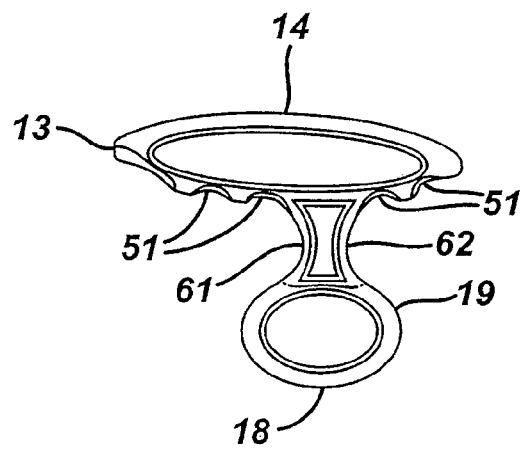
FIG. 5 is a side view of the invention.

FIG. 5 shows a side view of the vascular compression apparatus 10. This illustrates more clearly the convex nature of the pad 11 bottom 18. A series of optional grooves 51 are shown on the bottom side 22 of the handle 13. These grooves allow the user to place their fingers on the bottom side 22 of the handle 13 to either assist in rocking the device or aid in applying additional downward pressure on the pad in a manner that provides for additional stability of the device. The shaft 12 has a distal or front side 61 and a proximal or rear side 62. In a preferred embodiment, sides 61 and 62 are concave.

Figure 6:
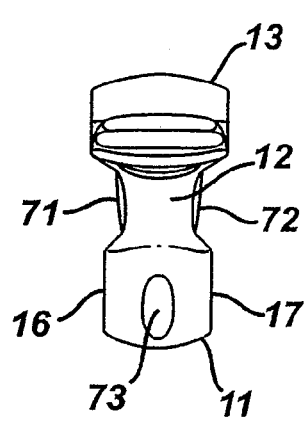
FIG. 6 is a front view of the invention.

FIG. 6 shows a front view of the vascular compression apparatus 10. The front of the device is oriented so that it is oriented distally and faces the patient's feet. The pad 11 contains a groove 73 which can be used to help guide the removal of the catheter. The groove is oriented approximately medially to the pad and generally distally. Sides 71 and 72 of the handle may be solid or as pictured substantially hollow to save on weight. In addition, the pad 11 has sides 16 and 17 which may be solid or, as pictured, substantially hollow.

The vascular compression device is generally molded of a mostly rigid material, for example, an acrylic or a plastic. The only requirement is that the material is sturdy enough to withstand the application of downward pressure onto a human patient, sufficient to cause a complete occlusion of an artery. The vascular compression apparatus 10 may be packaged and sterilized as a sterile medical product so that the user need not clean or wash it prior to its use. In a preferred embodiment the material is transparent so that the user can more easily align the device with the wound, the relevant artery or vein and/or the catheter or cannula being removed.

The pad 11, in a preferred embodiment, when viewed from the side is shaped as an oval knob, preferably having open or recessed sides and a generally constant dimension between the side surfaces of the pad 11.

The handle 13 is generally somewhat elongated. This shape enables a user to place the base of the palm of their hand directly over the topmost area of the handle 13 and, bending their wrist so that the palm of their hand faces downward. By keeping their elbow straight, they can comfortably apply pressure downwards without significant exertion of muscles in the forearm, wrist or hand while maintaining a relatively stable attitude of the vascular compression apparatus 10.

The proximal end of the shaft 12 connects to the handle 11 generally off-center of the bottom 22 of the handle 13. In a preferred embodiment, the shaft 12 may have a front 61 and back 62 that are convex. The sides 71 and 72 of the shaft 12 can be either solid or partially hollow to reduce the weight of the device. The length of the shaft 12 is at least sufficient to provide ample space for motion of the user's fingers when using the vascular compression apparatus 10 on a patient, but not so long that it inhibits the user's ability to maintain a generally straight elbow and stable attitude in the application of downward pressure.

In prior art devices the pad is generally placed proximal to the catheter insertion site and over the blood vessel containing the catheter. The catheter or cannula is then removed from the blood vessel and pressure applied to the handle by the user in a downward direction to force the pad to compress the blood vessel for the purpose of controlling bleeding and, farther, to achieve hemostasis.

In the device of the invention the convex pad bottom 18 as well as the off-center placement of the shaft 12, relative to the attached handle 13 permit easy rocking of the device both proximally and distally from the puncture or wound site allowing for control of blood flow both before and after removal of a catheter, or similar device. Specifically, a user would place the device 10 over a catheter insertion site and parallel to the blood vessel containing the catheter preferably by positioning the device using the guides 32 and 33 and aligning the device using the vessel alignment guide 31.

The user would then apply downward pressure from the shoulders onto the handle 13 and through the shaft 12 while rocking the device 10 proximally along the blood vessel. The user would then retrieve the catheter or cannula from the puncture site. The user would then rock the device 10 distally towards and optionally over the puncture site while still exerting sufficient downward pressure to achieve hemostasis.

In another alternative embodiment, the handle 13 and shaft 12 of the vascular compression apparatus 10 may be formed as a single member, to which the pad 11 may be removably connected by the user prior to use. In a further alternative embodiment the removeable pad is disposable. Methods for attaching disposable pads to vascular compression devices are well known in the art and have been described by Toller in U.S. Pat. No. 5,342,388 and Royce in U.S. Pat. No. 4,572,182, which disclosures are hereby incorporated by reference.

The invention further contemplates a pad 11 for a vascular compression device 10 that is substantially convex. In particular, a pad for a manual vascular compression device which is convex.

In another alternative embodiment, certain portions of the vascular compression apparatus may be treated or have applied to it a material to modify the coefficient of friction of the surfaces to which such treatment or material is applied. An application of this treatment or material has the effect of minimizing or eliminating slippage so that post-catheterization complications at the puncture site are avoided, where such treatment or material is applied to the bottom surface 18 of the pad 11. Such treatment or material may also prevent slippage of the vascular compression apparatus in the user's hand, also helping to prevent slippage or other undesired movement on the patient's body surface, where such treatment or material is applied to the top surface of the handle 13.

In another alternative embodiment, certain portions of the bottom 22 of the handle 13 of the vascular compression apparatus 10 may be modified to contain grooves 51 for the optional placement of the user's fingers. The ability for the user to place their fingers directly on the pad, further minimizes or eliminates the possibility of slippage, and provides for better control of the device so that post-catheterization complications at the puncture site are avoided.

In another alternative embodiment, the composition of the vascular compression apparatus 10 may be changed to a heavier material, or material may be added to portions of the vascular compression apparatus to make it sufficiently heavy to achieve partial or total occlusion of a blood vessel with little or no exertion of downward pressure on the handle 13.

This detailed description of the invention is for illustrative purposes only. A reading by those skilled in the art will bring to mind various changes without departing from the spirit and scope of the invention.

What is claimed is:

1. A handheld vascular compression apparatus for applying pressure to tissue in proximity to a puncture site in a body surface and a blood vessel; the handheld vascular compression apparatus comprising:

(a) a handle for manually operating the handheld vascular compression apparatus;

(b) a shaft extending generally perpendicularly from the handle; and (c) a pad having a long axis and a short axis and having a top side and a bottom side and connected on the top side to and extending from a distal end of the shaft through a center of gravity of the handle, wherein the pad, when viewed from the side, is shaped as an oval knob and has a convex bottom side to make contact with the body surface;

wherein the apparatus is made of mostly rigid material that is sturdy enough to withstand the application of downward pressure sufficient to cause a complete occlusion of an artery;

wherein the handle and shaft are formed as a single member;

wherein a proximal end of the shaft is connected to the handle at a point off center of a bottom side of the handle; and wherein the pad is rigidly connected to the shaft such that the handheld vascular compression apparatus is configured to be operated by manually moving the handle to thereby rock the pad along the body surface in a first direction to allow a catheter to be removed, and in a second opposed direction to provide compression along an angle of the catheter track from the body surface to the blood vessel.

2. The handheld vascular compression apparatus as recited in claim 1 wherein the apparatus is made from a material that is transparent.

3. The handheld vascular compression apparatus as recited in claim 1 wherein portions of the surface of the handheld vascular compression apparatus are modified by one or more means selected from the group comprising incorporation of a different material, overmolding using a different material, a surface treatment, a surface texture, and a coating; the portions of the surface thereby having a different coefficient of friction than the surfaces of other portions of the vascular compression apparatus.

4. The handheld vascular compression apparatus as recited in claim 1 wherein the apparatus is configured to be used for femoral compression.

5. The handheld vascular compression apparatus as recited in claim 1 wherein the topside of the pad is formed to receive one or more fingers.

6. A vascular compression apparatus for applying pressure to tissue in proximity to a puncture site in a body surface and a blood vessel; the vascular compression apparatus comprising:
   (a) a handle;
   (b) a shaft extending generally perpendicularly from the handle;
   (c) an oval pad having a top side and a bottom side and connected on the top side to a distal end of the shaft wherein the pad has a convex bottom side, which makes contact with the body surface; and
   (d) a groove for guiding a catheter formed in a surface of the convex bottom side of the pad and extending less than the entire height of the pad;

wherein the apparatus is made of mostly rigid material that is sturdy enough to withstand the application of downward pressure sufficient to cause a complete occlusion of an artery;

wherein the handle and shaft are formed as a single member; and wherein the device is configured to allow a user to rock the pad proximally, for proximal control of blood flow while retrieving a device from a puncture site, followed by distal rocking of the device to the puncture site to achieve hemostasis.

7. The apparatus of claim 6 wherein the oval pad has open or recessed sides and a generally constant dimension between the side surfaces of the pad.

8. A manual vascular compression apparatus for applying pressure to tissue in proximity to a puncture site in a body surface and a blood vessel; the vascular compression apparatus comprising:
   (a) a handle;
   (b) a shaft extending generally perpendicularly from the handle;
   (c) a pad having a top side and a bottom side and connected to the shaft on a top side at a distal end from the handle wherein the pad when viewed from the side is shaped as an oval knob and has a convex bottom side, which makes contact with the body surface; and
   (d) a vessel alignment guide comprising one or more markings disposed on a top surface of the handle for aligning the apparatus with a blood vessel.

9. The apparatus of claim 8, wherein the apparatus is made from a transparent material.

10. The apparatus of claim 8, wherein the pad comprises a groove for guiding a catheter.

11. The apparatus of claim 8, wherein the one or more markings include a line for alignment with the orientation of the blood vessel.

12. The apparatus of claim 11, wherein the apparatus is asymmetric and the one or more markings include indications as to the orientation of the apparatus along the blood vessel.

* * * * *